United States Patent
Bieger et al.

(10) Patent No.: US 6,690,964 B2
(45) Date of Patent: Feb. 10, 2004

(54) METHOD AND DEVICE FOR VISUALIZATION OF POSITIONS AND ORIENTATION OF INTRACORPOREALLY GUIDED INSTRUMENTS DURING A SURGICAL INTERVENTION

(75) Inventors: Johannes Bieger, Erlangen (DE); Rainer Graumann, Hoechstadt (DE); Norbert Rahn, Forchheim (DE)

(73) Assignee: Siemens Aktiengesellschaft, Münich (DE)

( * ) Notice: Subject to any disclaimer, the term of this patent is extended or adjusted under 35 U.S.C. 154(b) by 0 days.

(21) Appl. No.: 09/898,592

(22) Filed: Jul. 3, 2001

(65) Prior Publication Data

US 2002/0077533 A1 Jun. 20, 2002

(30) Foreign Application Priority Data

Jul. 12, 2000 (DE) .......................................... 100 33 723

(51) Int. Cl.⁷ ................................................ A61B 5/05
(52) U.S. Cl. ...................... 600/424; 600/427; 600/407
(58) Field of Search ....................... 345/7, 8, 9; 348/51, 348/77; 600/473, 117, 407, 417, 420, 421, 424, 425, 414, 426, 411, 427, 429, 416, 410, 431, 439, 476, 477; 606/130; 356/625, 626, 627, 628

(56) References Cited

U.S. PATENT DOCUMENTS

| | | | | |
|---|---|---|---|---|
| 4,535,782 A | * | 8/1985 | Zoltan ........................ 600/477 |
| 5,526,812 A | * | 6/1996 | Dumoulin et al. ........... 600/407 |
| 5,638,819 A | * | 6/1997 | Manwaring et al. ......... 600/424 |
| 5,694,142 A | | 12/1997 | Dumoulin et al. |
| 5,772,593 A | * | 6/1998 | Hakamata .................... 600/407 |
| 5,967,979 A | * | 10/1999 | Taylor et al. ................ 600/407 |
| 6,129,668 A | * | 10/2000 | Haynor et al. ............... 600/424 |
| 6,216,029 B1 | * | 4/2001 | Paltieli ........................ 600/427 |
| 6,314,311 B1 | * | 11/2001 | Williams et al. ............. 600/425 |
| 2002/0016539 A1 | * | 2/2002 | Michaelis et al. ........... 600/407 |

FOREIGN PATENT DOCUMENTS

WO    WO 97/29709    8/1997

* cited by examiner

*Primary Examiner*—Eleni Mantis Merlader
(74) *Attorney, Agent, or Firm*—Schiff Hardin & Waite

(57) ABSTRACT

In a visualization system and method for visualization of data that relate to a medical intervention at a patient, a surgeon has no visual contact with a surgical instrument but can visualize in the form of a projected geometrical shape by a visualization device, the geometrical shape corresponding to the position and orientation of the surgical instrument onto the body surface of the patient under which the surgical instrument is located with a characteristic of the geometrical shape indicating the distance of the surgical instrument from the body surface.

6 Claims, 2 Drawing Sheets

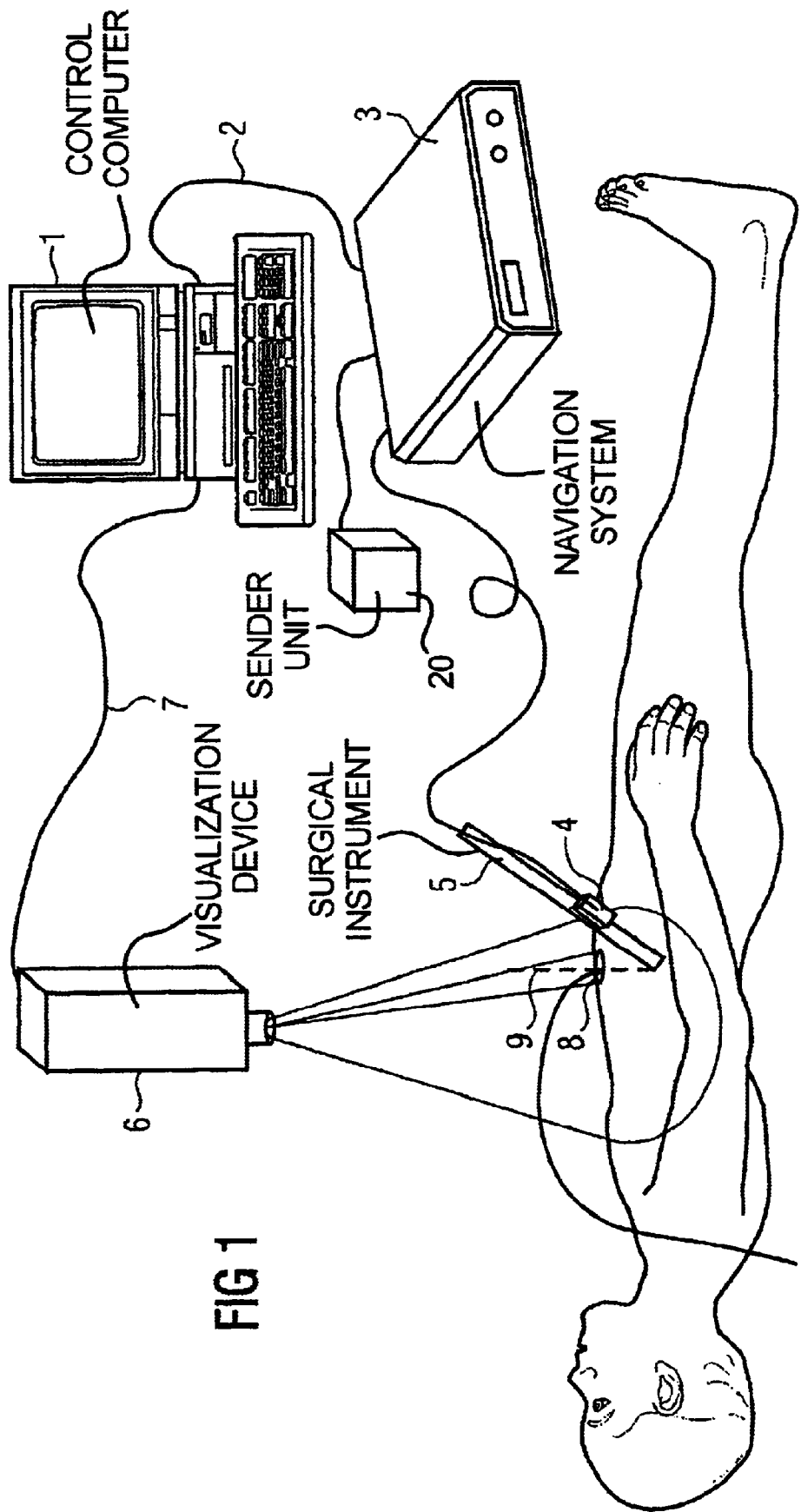

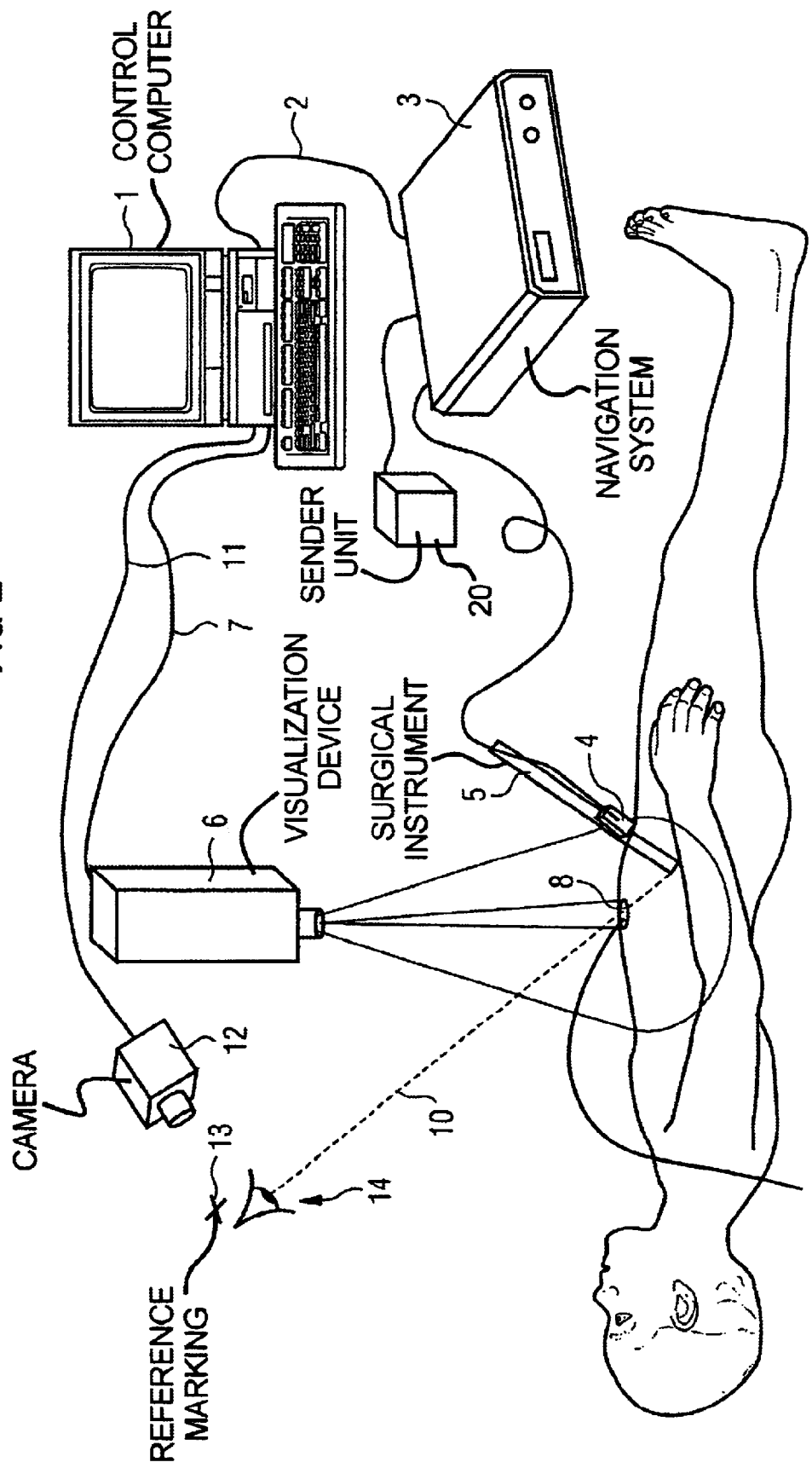

METHOD AND DEVICE FOR VISUALIZATION OF POSITIONS AND ORIENTATION OF INTRACORPOREALLY GUIDED INSTRUMENTS DURING A SURGICAL INTERVENTION

BACKGROUND OF THE INVENTION

1. Field of the Invention

The present invention is directed to a visualization device for the visualization of data that relate to a medical intervention at a patient, as well as to a method for the visualization of data that relate to a medical intervention at a patient.

2. Description of the Prior Art

In medical or surgical interventions, the position and orientation of surgical instruments that, for example, can be equipped with sensors of a navigation system for determining the position and orientation can be displayed as medical image data during the surgical intervention.

In specific fields of employment, there is, the necessity of employing a number of surgical instruments that are intracorporeally guided in the patient and that cannot be visually tracked as a group by the surgeon. Such a situation occurs, for example, in some gastroenterological laparoscopy interventions wherein a surgical instrument introduced into the abdominal cavity should be guided to the same position at which an endoscope introduced into the colon is located. It is not easy for the surgeon to accomplish this since there is no visual contact with the guided instruments.

The document, "Medical Procedures and Apparatus Using Intrabody Probes" (WO97/29709), discloses the employment of a number of sensors for the visualization of the surgical instruments in detail. The user interface for visualization of the instrument positions (with the assistance of one or more monitors and with the assistance of "Virtual Reality Devices") is also disclosed therein; the instruments are thereby visualized on a planar computer display.

A disadvantage of this arrangement is that the visualization of the surgical instruments is not especially intuitive on a planar computer display. Moreover, it is inconvenient for the surgeon to constantly change the direction of view between the computer display and the operation field during the intervention. Additionally, the spatial conditions in an operating room are very constricted and therefore a minimization of components (for example, avoiding the presence of the computer display in the indicated case) is desirable.

U.S. Pat. No. 5,694,142 discloses a solution wherein the surgeon views his operating field through a semi-transparent pane, with the medical image data are displayed on into this semi-transparent pane and thus are superimposed on the view of the operation field.

SUMMARY OF THE INVENTION

An object of the present invention is to provide a visualization device and a method for the visualization of data that relate to a medical or, respectively, surgical intervention at a patient which achieves the following:

The position and orientation of instruments with which there is no visual contact are visualized.

The position and orientation of a number of instruments with which there is no visual contact are visualized relative to one another.

The visualization is undertaken such that the surgeon need not avert his or her eyes from the operation field during the intervention.

The visualization ensues relative to the patient (i.e. in the patient coordinate system and not in a coordinate that is specific to the image data).

This object is achieved by a visualization device for the visualization of data that relate to a medical intervention at a patient wherein the visualization device projects the data onto the body surface of the patient, for example by light projection.

This object is also achieved by a method for the visualization of data that relate to a medical intervention at a patient, whereby the data are projected onto the body surface of the patient.

According to the present invention, the data are projected onto the body surface in the region of the intervention. In a gastroenterological, laparoscopic intervention, the projection ensues, for example, onto the upper abdomen of the patient. The surgeon thus can acquire operation-related data without having to avert his or her eyes from the operation field.

Further, components such as for example, the computer display are eliminated.

In an embodiment of the present invention, data that relate to the position and orientation of one or more intracorporeally guided instruments are projected onto the body surface of the patient.

These data are advantageously projected onto the body surface of the patient as geometrical shape or figure, for example a circle and/or as arrow, in a specific relationship to the position of the surgical instrument, with the geometrical shape moving on the body surface of the patient together with the movement of the instruments. During the intervention, the surgeon thus can track the position and orientation of one or more instruments with which he or she has no direct visual contact without having to avert his or her eyes from the operation field. The orientation can, for example, be presented by the arrow direction.

The problem of bringing a number of instruments together (for example, endoscope and surgical instrument), with which there is no direct visual contact, is reduced in this procedure to the superimposition of geometrical shapes that are projected onto the body surface of the patient.

According to the present invention, the projection of the position and orientation of the surgical instruments or of the geometrical shapes can be implemented in the patient coordinate system, i.e., the position and orientation are projected exactly onto the location of the body surface under which the surgical instrument is in fact located.

A projection of the geometrical shape exactly perpendicularly above the position of the surgical instrument in the body of the patient would thereby also be conceivable, in which case the instrument positions projected onto the body surface of the patient always lie on a vertical connecting line between the actual and the projected position of the surgical instrument. Given this type of projection, however, the point of view or the line of vision of the intervening surgeon is not addressed.

In order to address the line of vision of the surgeon, the geometrical shape is projected onto the body surface at an angle relative to the position of the surgical instrument in viewing direction of the intervening surgeon. This means that the location of the projection of the geometrical shape on the body surface is located on the connecting line between the actual spatial position of the surgical instrument and the line of vision of the surgeon onto the instrument. In order to be able to define the starting point of this line of vision of the surgeon, one or more reference markings are attached to or in the proximity of the head of the surgeon, the spatial positions of the one or more reference markings being respectively communicated to a navigation computer that also determines the positions and or orientations of the surgical instruments before renewed projected of the positions of the instruments. The head of the surgeon thus is continuously tracked, for example with a stereo camera, and the position thereof is thus acquired.

For example, one or more cross-shaped reference markings are attached for this purpose to the operation cap of the surgeon, these being continuously detected by two cameras (stereo cameras) or when needed. In this way, the coordinates of the head of the surgeon are determined.

In order, in addition to the head position, to also be able to determine the orientation of the head and, thus, the viewing direction thereof, a number of reference markings attached to the head or to the operating cap are detected. Subsequently, the position of the instrument is projected onto the body surface of the patient as the intersection between the position of the reference markings at the head of the surgeon and the actual instrument position, which is established by a sensor of a navigation system at the surgical instrument.

Since only a two-dimensional visualization of the instrument position or of the corresponding geometrical shape on the body surface of the patient is possible, the third spatial dimension, i.e. the perpendicular distance of the surgical instrument from the body surface, or from the patient support, and thus the "depth" of the surgical instrument, must be displayed encoded. This information can, for example, be displayed with a color and/or size coding. The annular or circular geometrical shapes for displaying the position or the arrow-geometrical shapes for displaying the orientation of a surgical instrument, accordingly change in color and/or in size dependent on the depth of the instrument in the body of the patient, i.e. dependent on the perpendicular distance from the body surface or from the patient support.

In a further embodiment of the present invention, medical image data of the patient are projected onto the body surface of the patient. For example, such data can be image data that are pre-operatively obtained, i.e. at an arbitrary time before the intervention. With this method, real-time image data such as, for example, 2D or 3D ultrasound image data or 2D or 3D x-ray image data obtained using a mobile C-bend x-ray system also can be projected onto the body surface of the patient.

Given this method, it can be just as advantageous to acquire the position of the head of the intervening surgeon in order to project the image data onto the body surface of the patient such that the anatomical structures images in the image data come to lie directly above the actual organ structures from the view point of the surgeon (and, thus, the line of vision of the surgeon).

It is also possible to gate the image data onto the body surface of the patient such that the middle projection line proceeds along the axis of an intracorporeally or extracorporeally guided surgical instrument that is equipped with position sensors of a navigation system for determining its orientation. Given a minimally invasive intervention, thus, an optimum introduction opening can be found by moving the surgical instrument over the patient surface. Organs or other essentially anatomical structures lying under the introduction opening thus can be recognized before the introduction by gating the medical image data onto the patient surface. In a further embodiment of the invention, data representing the results of an operation planning implemented before the operation such as, for example, organ, tissue or bone structures, position information about a lesion, planned operating paths, planned entry or target points, can be projected onto the body surface of the patient.

The gating of results of the operation planning onto the body surface of the patient can, for example, be in turn employed for determining an optimum entry point within the framework of minimally invasive interventions. When the projection of the results of the operation planning onto the body surface of the patient is combined with the projection of the position of surgical instruments, for example, one can replicate whether the guided instruments are moving on the operation paths defined in the operation planning.

It should be noted that the projection of positions and orientations of surgical instruments, the projection of medical data and the projection of results of a preceding operation planning onto the body surface of the patient can be implemented separately from one another or arbitrarily combined with one another.

Further, the patient anatomy must be taken into consideration for the projection, i.e. a matching between the body surface of the patient with the visualization device must be undertaken so that the data are projected in a correctly positioned manner on the body surface of the patient.

DESCRIPTION OF THE DRAWINGS

FIG. 1 shows an exemplary embodiment without taking the viewing direction of the intervening surgeon into consideration in the projection of the data.

FIG. 2 shows an exemplary embodiment taking the viewing direction of the intervening surgeon into consideration in the projection of the data.

DESCRIPTION OF THE PREFERRED EMBODIMENTS

FIG. 1 shows an exemplary embodiment of the present invention without taking the viewing direction of the intervening surgeon into consideration in the inventive projection of the data onto the body surface of the patient.

As shown in this Figure, a surgical instrument 5 is guided in the abdominal cavity of the patient. The surgical instrument 5 is provided with a position sensor 4 of an electromagnetic navigation system 3. With assistance of a sender unit 20 the navigation system 3 can determine the spatial coordinates of the position sensor 4 and thus of the surgical instrument 5. The spatial coordinates are communicated continuously or intermittently to a control computer 1 via an interface 2 for example, a serial interface. As soon as the control computer 1 acquires such a spatial coordinate of the instrument 5, it drives the inventive visualization device 6 such via a computer interface 7 that the position of the surgical instrument 5 is projected onto the body surface of the patient as a geometrical shape, being projected onto that location 8 lying vertically 9 above the instrument.

This projected, geometrical shape can be varied in shape, color and/or size in order to thus encode the depth information of the surgical instrument 5 or other properties of the instrument 5.

The inventive projection of the instrument position and orientations taking the patient anatomy into consideration assumes a registration between navigation system 3, projected system 6 and patient anatomy. In order to project the positions and orientations of the surgical instruments 5 onto the correct location 8 of the body surface of the patient.

FIG. 2 shows an exemplary embodiment to the present invention taking the viewing direction of an intervening surgeon into consideration in the projection of the data onto the body surface of the patient.

As already shown in FIG. 1, a surgical instrument 5 is guided in the abdominal cavity of the patient, the instrument 5 being again provided with a position sensor 4 of a navigation system 3 with which the spatial coordinates of the surgical instrument 5 are transmitted continuously or intermittently to the control computer 1 via an interface 2. In addition to the spatial coordinates of the surgical instrument 5, the spatial position and orientation of the head of the surgeon are also acquired with a stereo camera 12 that supplies position data to the control computer 1 via an interface 11 (for example, a frame grabber card or a parallel or serial interface). The head position 8 or head orientation, and thus the direction of view of the surgeon can be determined with one or more reference markings 13 registered continuously or as needed that, for example, can be attached to the head covering of the surgeon.

As soon as the control computer 1 has acquired a spatial coordinate of the instrument 5 as well as the head position/orientation or viewing direction of the surgeon, the control computer 1 drives the inventive visualization device 6 such via a computer interface 7 for example, a serial or parallel interface that the position of the surgical instrument 5 is projected onto the body surface of the patient such that the gated contour 8 is located on the connecting line 10 between the head of the surgeon 14 and the tip of the surgical instrument 5.

Although modifications and changes may be suggested by those skilled in the art, it is the intention of the inventors to embody within the patent warranted hereon all changes and modifications as reasonably and properly come within the scope of their contribution to the art.

We claim as our invention:

1. A system for visualization of data relating to a medical intervention at a patient, comprising a navigation system which monitors a direction of view of a surgeon operating a surgical instrument adapted to be guided in the body of the patient with which there is no visual contact and a projector adapted to project a geometrical shape corresponding to a position and orientation of the surgical instrument onto a body surface of the patient under which the surgical instrument is adapted to be located at an angle relative to the position of the surgical instrument in the direction of view, said projector projecting said geometrical shape with a characteristic of said geometrical shape, selected from the group consisting of color of said geometrical shape and size of said geometrical shape, representing a distance of said surgical instrument from the body surface.

2. A system for visualization as claimed in claim 1 wherein said projector is adapted to project medical image data, obtained from a medical imaging modality of the body surface in said medical image data representing the position and orientation of the surgical instrument.

3. A system for visualization as claimed in claim 1 wherein said projector is adapted to project data obtained from a preceding planning of said medical intervention on the body surface.

4. A method for visualizing data relating to a medical intervention at a patient, comprising the steps of monitoring a direction of view of a surgeon operating a surgical instrument adapted to be guided in the body of the patient with which there is no visual contact and projecting a geometrical shape corresponding to a position and orientation of the surgical instrument onto a body surface of the patient under which the surgical instrument is adapted to be located at an angle relative to the position of the surgical instrument in the direction of view projecting said geometrical shape with a characteristic of said geometrical shape, selected from the group consisting of color of said geometrical shape and size of said geometrical shape, representing a distance of said surgical instrument from the body surface.

5. A method for visualizing data as claimed in claim 4 comprising projecting medical image data, obtained from a medical imaging modality, onto the body surface of the patient in said medical image data representing the position and orientation of the surgical instrument.

6. A method for visualizing data as claimed in claim 4 comprising the further step of conducting a planning of said medical intervention preceding said medical intervention, to obtain planning data, and projecting said planning data onto the body surface of the patient.

\* \* \* \* \*